United States Patent

Denis et al.

[11] Patent Number: 5,811,550
[45] Date of Patent: Sep. 22, 1998

[54] PROCESS FOR THE PREPARATION OF A 1, 3-OXAZOLIDINE-5-CARBOXYLIC ACID

[75] Inventors: Jean-Noel Denis; Andrew-Elliot Greene, both of Uriage; Alice Kanazawa, Grenoble, all of France

[73] Assignee: Rhone-Poulenc Rorer, S.A., Antony Cedex, France

[21] Appl. No.: 897,650

[22] PCT Filed: Nov. 18, 1993

[86] PCT No.: PCT/FR93/01133

§ 371 Date: May 19, 1995

§ 102(e) Date: May 19, 1995

[87] PCT Pub. No.: WO94/12482

PCT Pub. Date: Jun. 9, 1994

Related U.S. Application Data

[63] Continuation of Ser. No. 424,501, filed as PCT/FR93/01133, Nov. 18, 1993 published as WO94/12482, Jun. 9, 1994, abandoned.

[30] Foreign Application Priority Data

Nov. 20, 1992 [FR] France .................................. 92 13939

[51] Int. Cl.$^6$ ................................................. C07D 263/06
[52] U.S. Cl. ........................... 544/137; 548/215; 549/510
[58] Field of Search ............................... 548/215; 544/137

[56] References Cited

U.S. PATENT DOCUMENTS

| | | | |
|---|---|---|---|
| Re. 34,277 | 6/1993 | Denis et al. | 549/510 |
| 4,162,251 | 7/1979 | Hiraoka et al. | 540/221 |
| 5,476,954 | 12/1995 | Bourzat et al. | 548/215 |
| 5,502,192 | 3/1996 | Ganci | 546/49 |
| 5,556,877 | 9/1996 | Bouchard | 549/511 |
| 5,571,917 | 11/1996 | Bouchard | 548/215 |
| 5,637,723 | 6/1997 | Commerson | 548/215 |
| 5,677,462 | 10/1997 | Mas | 548/215 |
| 5,717,103 | 2/1998 | Denis | 548/215 |
| 5,726,318 | 3/1998 | Denis | 548/215 |

FOREIGN PATENT DOCUMENTS

| | | | |
|---|---|---|---|
| WO 92/09589 | 6/1992 | WIPO | 549/510 |
| 94-07873 | 4/1994 | WIPO | 579/510 |
| 94-07876 | 4/1994 | WIPO | 549/510 |
| 94-07878 | 4/1994 | WIPO | 579/510 |
| 94-07879 | 4/1994 | WIPO | 549/510 |
| 94-12842 | 6/1994 | WIPO | |

Primary Examiner—Donald G. Daus
Attorney, Agent, or Firm—Finnegan, Henderson, Farabow, Garrett & Dunner, L.L.P.

[57] ABSTRACT

Method for the preparation of 1,3-oxazolidin 5-carboxylic acid having the general formula (I)

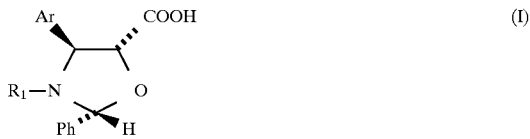

from a product having the general formula (II)

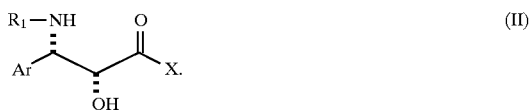

In the general formulas (I) and (II), Ar is an aryl radical, $R_1$ is a benzoyl radical or a radical $R_2$—O—CO— wherein $R_2$ is an alkyl, alkenyl, alkynyl, cycloalkyl, cycloalkenyl, bicycloalkyl, phenyl or heterocyclyl radical, Ph is an optionally substituted phenyl radical, X is the residue of an optically active organic base or an alkoxy radical optionally substituted by a phenyl radical. The acids of formulas (I) and (II) are particularly useful in preparing taxol, Taxotere or analogs thereof which have remarkable antitumor and antileukemia properties.

9 Claims, No Drawings

PROCESS FOR THE PREPARATION OF A 1, 3-OXAZOLIDINE-5-CARBOXYLIC ACID

This application is a continuation, of application Ser. No. 08/424,501, filed as PCT/FR93/01133, Nov. 18, 1993 published as WO94/12482, Jun. 9, 1994, now abandoned.

DESCRIPTION OF THE INVENTION

The present invention relates to a process for the preparation of a 1,3-oxazolidine-5-carboxylic acid of general formula:

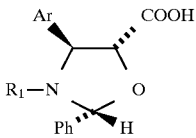

in which Ar represents an aryl radical, $R_1$ represents a benzoyl radical or a radical $R_2$—O—CO— in which $R_2$ represents an alkyl, alkenyl, alkynyl, cycloalkyl, cycloalkenyl, bicycloalkyl, phenyl or nitrogenous heterocyclyl radical, and Ph represents an optionally substituted phenyl radical.

More particularly, Ar represents a phenyl or α- or β-naphthyl radical optionally substituted by one or a number of atoms or radicals, which are identical or different, chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoycarbonylamino, amino, alkylamino, dialkylamino, carboxyl, alkoxycarbonyl, carbamoyl, dialkylcarbamoyl, cyano and trifluoromethyl radicals, it being understood that the alkyl radicals and the alkyl portions of the other radicals contain 1 to 4 carbon atoms, the alkenyl and alkynyl radicals contain 3 to 8 carbon atoms and the aryl radicals are phenyl or α- or β-naphthyl radicals, $R_1$ represents an optionally substituted benzoyl radical or a radical $R_2$—O—CO— in which $R_2$ represents a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals optionally being substituted by one or a number of substituents chosen from halogen atoms and hydroxyl, alkyloxy containing 1 to 4 carbon atoms, dialkylamino, in which each alkyl part contains 1 to 4 carbon atoms, piperidino, morpholino, 1-piperazinyl (optionally substituted in the 4-position by an alkyl radical containing 1 to 4 carbon atoms or by a phenylalkyl radical in which the alkyl part contains 1 to 4 carbon atoms), cycloalkyl containing 3 to 6 carbon atoms, cycloalkenyl containing 4 to 6 carbon atoms, phenyl, cyano, carboxyl or alkyloxycarbonyl, in which the alkyl part contains 1 to 4 carbon atoms, radicals, or a phenyl radical optionally substituted by one or a number of atoms or radicals chosen from alkyl radicals containing 1 to 4 carbon atoms or alkyloxy radicals containing 1 to 4 carbon atoms, or a saturated or unsaturated nitrogenous heterocyclyl radical containing 5 or 6 members and optionally substituted by one or a number of alkyl radicals containing 1 to 4 carbon atoms, it being understood that the cycloalkyl, cycloalkenyl or bicycloalkyl radicals can be optionally substituted by one or a number of alkyl radicals containing 1 to 4 carbon atoms, and Ph represents a phenyl radical substituted by one or a number of electron-donating radicals chosen more particularly from the group of alkoxy radicals containing 1 to 4 carbon atoms.

According to the present invention, an acid of general formula (I) can be obtained by cyclization of a product of general formula:

in which Ar, $R_1$ and Ph are defined as above and X represents a

residue of an optically active organic base or a residue —O—R in which R represents an alkyl radical containing 1 to 4 carbon atoms optionally substituted by a phenyl radical, followed by hydrolysis or saponification of the product obtained of general formula:

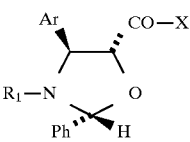

in which Ar, $R_1$, Ph and X are defined as above.

Generally, the cyclization is performed by carrying out the reaction, preferably in anhydrous medium, in an organic solvent chosen from ethers, esters, ketones, nitriles, optionally halogenated aliphatic hydrocarbons and optionally halogenated aromatic hydrocarbons in the presence of an oxidizing agent such as dichlorodicyanobenzoquinone at a temperature between 0° C. and the boiling temperature of the reaction mixture. Preferably, the reaction is carried out in a halogenated aliphatic hydrocarbon at a temperature in the region of 20° C.

The product of general formula (III) in which X represents a

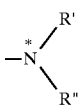

residue which is, preferably, an L-(+)-2,10-camphorsultam residue of formula:

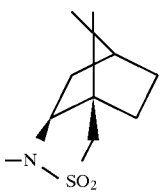

is hydrolyzed to an acid of general formula (I) by means of an inorganic base such as sodium hydroxide, potassium hydroxide or lithium hydroxide in aqueous or aqueous/organic medium. It is particularly advantageous to carry out the reaction in a tetrahydrofuran/water mixture in the presence of hydrogen peroxide. The reaction temperature is generally between −10° and 20° C. and preferably in the region of 0° C.

The product of general formula (III) in which X represents a —O—R residue is saponified to the acid of general formula (I) by means of an inorganic base such as an alkali metal (lithium, potassium, sodium) hydroxide, an alkali metal carbonate or bicarbonate (sodium bicarbonate, potassium carbonate or bicarbonate) in aqueous/alcohol medium such as a methanol/water mixture at a temperature between 10° and 40° C., preferably in the region of 20° C.

The product of general formula (II) in which X represents a

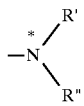

residue can be obtained by reacting an N-carbonylarylimine of general formula:

Ar—CH=N—R₁ (V)

in which Ar and $R_1$ are defined as above, with the anion of an optically active amide of a protected hydroxyacetic acid of general formula:

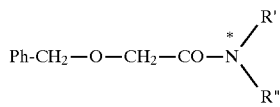 (VI)

in which Ph and

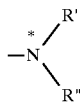

are defined as above.

Generally, the N-carbonylarylimine of general formula (V), optionally prepared in situ, is reacted with the amide of the hydroxyacetic acid, anionized beforehand, of general formula (VI) by means of an alkali metal amide. It is possible to mention, among the suitable amides, sodium bis(trimethylsilyl)amide (NHMDS), lithium bis (trimethylsilyl)amide (LHMDS) or potassium bis (trimethylsilyl)amide (KHMDS), lithium diisopropylamide (LDA), lithium diethylamide (LDEA), lithium dicyclohexylamide (LDCHA) and $(CH_3)_3SiN(R''')Li$ ($R'''$=alkyl, cycloalkyl, aryl). t-BuLi may also be mentioned. Lithium bis(trimethylsilyl)amide is very particularly advantageous as it makes it possible to obtain a high yield and excellent selectivity.

The N-carbonylarylimine of general formula (V) can be obtained by reacting an optionally substituted benzoyl halide or a reactive derivative of general formula:

$R_2$—O—CO—Y (VII)

in which $R_2$ is defined as above and Y represents a halogen (fluorine, chlorine) atom or a —O—$R_2$ or —O—CO—$OR_2$ residue, with a product of general formula:

Ar—CH=N—Z (VIII)

in which Ar is defined as above and Z represents a reactive group such as a trialkylsilyl radical like the trimethylsilyl radical.

Generally, the reaction of the optionally substituted benzoyl halide or of the products of general formula (VII) with the product of general formula (VIII) is carried out by heating in an organic solvent such as an ester, for example ethyl acetate, or a halogenated aliphatic hydrocarbon, for example dichloromethane or chloroform, or an aromatic hydrocarbon, for example toluene or benzene.

The imine of general formula (VIII) can be obtained from the aldehyde of general formula:

Ar—CHO (IX)

in which Ar is defined as above, according to known methods. For example, a product of general formula (VIII) in which Z represents a trimethylsilyl radical can be obtained according to D. J. Hart et al., J. Org. Chem., 48, 289 (1983) by reacting lithium bis(trimethylsilyl)amide (LHMDS), optionally prepared in situ by reacting butyllithium with bis(trimethylsilyl)amine, with the corresponding aldehyde of general formula (IX).

The imine of general formula (V) can also be prepared from the product of general formula:

 (X)

in which Ar and $R_1$ are defined as above, $Ph_1$ represents a phenyl radical optionally substituted, for example, by a methyl radical and n is equal to 0 or 2.

The imine of general formula (V) can be prepared in situ by reacting a strong base such as an amide, for example lithium bis(trimethylsilyl)amide, with a product of general formula (X) in which n is equal to zero.

The imine of general formula (V) can be prepared by the action of a base such as sodium or potassium carbonate in an organic solvent chosen from ethers such as tetrahydrofuran and aromatic hydrocarbons such as benzene or toluene at a temperature between 50° and 100° C.

The product of general formula (X) in which n is equal to 2 can be prepared by reacting an alkali metal sulphinate such as sodium or potassium phenylsulphinate with a mixture of an aldehyde of general formula (IX) in which Ar is defined as above and an amide of general formula:

$H_2N$—$R_1$ (XI)

in which $R_1$ is defined as above, the reaction being carried out in an aqueous/organic medium such as a mixture of water and an aliphatic alcohol containing 1 to 3 carbon atoms (methanol, ethanol) in the presence of an acid such as formic acid.

The optically active amide of general formula (VI) can be obtained by reacting an activated derivative of a protected hydroxyacetic acid of general formula:

Ph—$CH_2$—O—$CH_2$—COOH (XII)

in which Ph is defined as above, optionally in the salt, halide or anhydride form, with the corresponding, optionally anionized, nucleophilic base.

The product of general formula (XII) can be obtained by reacting a metal alkoxide of general formula:

Ph—$CH_2$—OM (XIII)

in which Ph is defined as above and M represents an alkali metal atom chosen from sodium, potassium and lithium, with an acid of general formula:

Hal—$CH_2$—COOH (XIV)

optionally in the alkali metal salt form, in which Hal represents a halogen atom preferably chosen from chlorine and bromine atoms.

Generally, the reaction is carried out in an organic solvent chosen from ethers such as tetrahydrofuran, amides such as dimethylformamide and aromatic hydrocarbons such as toluene and their mixture at a temperature between 20° C. and the reflux temperature of the reaction mixture.

The product of general formula (XII), in the halide form, can be obtained by reacting thionyl chloride or oxalyl chloride with the corresponding acid, the reaction being carried out in an inert organic solvent such as an aliphatic hydrocarbon, for example hexane, or an aromatic hydrocarbon, for example benzene or toluene, at a temperature in the region of 20° C.

The product of general formula (II) in which X represents a —O—R residue can be obtained, optionally in situ, by reacting an imidate of general formula:

(XV)

in which $R_3$ represents an alkyl radical containing 1 to 3 carbon atoms and optionally substituted by one or a number of halogen atoms, preferably a trichloromethyl radical, and Ph is defined as above, with an ester of general formula:

(XVI)

in which Ar, $R_1$ and R are defined as above.

Generally, the reaction is carried out in an organic solvent or a mixture of organic solvents chosen from optionally halogenated aliphatic hydrocarbons and cycloaliphatic hydrocarbons at a temperature between 0° and 50° C., preferably in the region of 20° C.

The ester of general formula (XVI) can be obtained by acylation of a phenylisoserine derivative of general formula:

(XVII)

in which Ar and R are defined as above, by means of optionally substituted benzoyl chloride or of a reactive derivative of general formula (VII), the reaction being carried out in an organic solvent, such as an aliphatic ester, for example ethyl acetate, or a halogenated aliphatic hydrocarbon, for example dichloromethane, or optionally in water, in the presence of an inorganic base such as sodium bicarbonate or of an organic base such as triethylamine.

Generally, the reaction is carried out at a temperature between 0° and 50° C., preferably in the region of 20° C.

The product of general formula (XVII) can be obtained under the conditions described in International Application PCT WO 92/09589 which is a counterpart of U.S. Pat. No. 5,476,954.

The product of general formula (II) in which X represents a —O—R residue can also be obtained from a product of general formula (II) in which X represents a

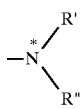

residue. To this end, the product of general formula (II) in which X represents a

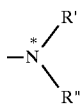

residue is hydrolyzed under the conditions described above for the hydrolysis of a product of general formula (III) to provide the acid of general formula:

(XVIII)

in which Ar, $R_1$ and Ph are defined as above, which is esterified, according to known methods, to give the product of general formula (II) in which X represents an —O—R residue.

According to the present invention, the acid of general formula (I) can also be obtained by reacting an ether of general formula:

$$Ph-CH_2-O-R_3 \qquad (XIX)$$

in which Ph is defined as above and $R_3$ represents an alkyl radical containing 1 to 4 carbon atoms or an aryl radical, with a phenylisoserine derivative of general formula (XVI), preferably in the 2R, 3S form, the reaction being carried out in anhydrous medium in an organic solvent chosen from ethers, esters, ketones, nitrites, optionally halogenated aliphatic hydrocarbons and optionally halogenated aromatic hydrocarbons in the presence of an oxidizing agent such as dichlorodicyanobenzoquinone at a temperature between 0° C. and the boiling temperature of the reaction mixture, followed by saponification in basic medium of the ester of general formula (III) thus obtained.

The process according to the invention makes it possible to obtain the acid of general formula (I) virtually free of its epimer of general formula:

(XX)

in which Ar, $R_1$ and Ph are defined as above.

It results therefrom that the acid of general formula (I) makes it possible to prepare the taxane derivatives of general formula:

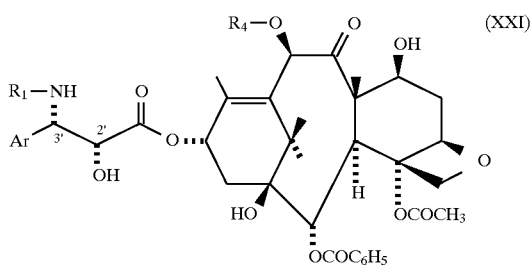

in which Ar and $R_1$ are defined as above and $R_4$ represents a hydrogen atom or an acetyl radical, virtually free of the 2'-epimer.

The taxane derivatives of general formula (XXI) can be obtained by:

condensation of an acid of general formula (I), or of a derivative of this acid, with bacccatin III or 10-deacetylbaccatin III of general formula:

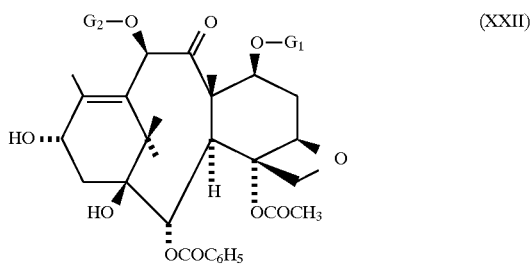

in which $G_1$ represents a protective group of the hydroxyl functional group and $G_2$ represents an acetyl radical or a protective group of the hydroxyl functional group, to obtain a product of general formula:

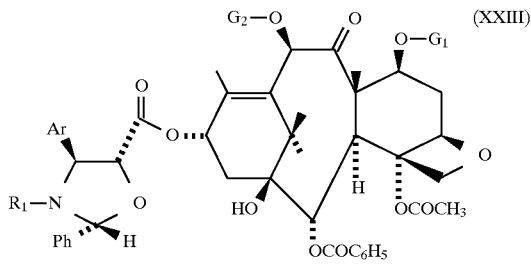

in which Ar, $R_1$, Ph, $G_1$ and $G_2$ are defined as above, deprotection of the side chain and optionally of the hydroxyl functional groups protected by $G_1$ and $G_2$ to obtain a product of general formula:

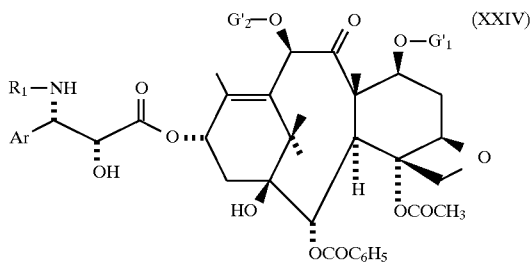

in which Ar and $R_1$ are defined as above, $G'_1$ represents a hydrogen atom or a protective group of the hydroxyl functional group and $G'_2$ represents a hydrogen atom or an acetyl radical or a protective group of the hydroxyl functional group, then optionally replacement of the $G'_1$ and optionally $G'_2$ protective groups of the product of general formula (XXIV) by hydrogen atoms to obtain a product of general formula (XXI).

The esterification of the product of general formula (XXII) is carried out by means of an acid of general formula (I), optionally in the anhydride form or in the halide or mixed anhydride form.

Preferably, an acid of general formula (I), or its activated derivatives, is used in which Ph represents a phenyl radical optionally substituted by one or a number of electron-donating radicals chosen more particularly from the group of alkoxy radicals containing 1 to 4 carbon atoms.

Esterification by means of an acid of general formula (I) can be carried out in the presence of a condensation agent such as a carbodiimide such as dicyclohexylcarbodiimide or a reactive carbonate such as di-2-pyridyl ketone and of an activating agent such as an aminopyridine such as 4-dimethylaminopyridine or 4-pyrrolidinopyridine, esterification being carried out in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitrites such as acetonitrile, aliphatic hydrocarbons such as pentane, hexane or heptane, halogenated aliphatic hydrocarbons such as dichloromethane or 1,2-dichloroethane or aromatic hydrocarbons such as benzene, toluene, xylenes, ethylbenzene, isopropylbenzene or chlorobenzene at a temperature between −10° and 90° C. It is particularly advantageous to carry out the esterification in an aromatic solvent at a temperature in the region of 20° C.

The esterification can also be carried out by using the acid of general formula (I) in the anhydride form of formula:

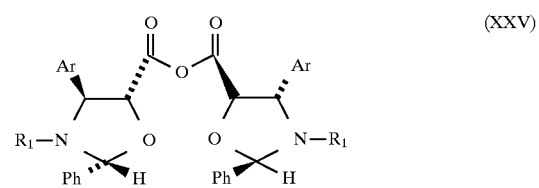

in which Ar, $R_1$ and Ph are defined as above, in the presence of an activating agent such as an aminopyridine such as 4-dimethylaminopyridine, the esterification being carried out in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane or aromatic hydrocarbons such as benzene, toluene, xylenes, ethylbenzene, isopropylbenzene or chlorobenzene at a temperature between 0° and 90° C.

The esterification can also be carried out by using the acid of general formula (I) in the halide form or in the mixed anhydride form of general formula:

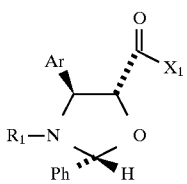 (XXVI)

in which Ar, $R_1$ and Ph are defined as above and $X_1$ represents a halogen atom or an acyloxy or aroyloxy radical, optionally prepared in situ, in the presence of a base which is preferably a nitrogenous organic base such as a tertiary aliphatic amine such as triethylamine, pyridine, an aminopyridine such as 4-dimethylaminopyridine or 4-pyrrolidinopyridine, the esterification being carried out an inert organic solvent chosen from ethers such as tetrahydrofuran, diisopropyl ether, methyl t-butyl ether or dioxane, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropyl-benzene or chlorobenzene at a temperature between 10° and 80° C., preferably in the region of 20° C.

Preferably, an activated derivative of general formula (XXVI), in which $X_1$ represents a halogen atom or an acyloxy radical containing 1 to 5 carbon atoms or an aroyloxy radical in which the aryl part is a phenyl radical optionally substituted by 1 to 5 atoms or radicals, which are identical or different, chosen from halogen atoms (chlorine, bromine) and the nitro, methyl or methoxy radicals, is used.

The deprotection of the side chain can be carried out in the presence of an inorganic acid (hydrochloric acid, sulphuric acid) or organic acid (acetic acid, methanesulphonic acid, trifluoromethanesulphonic acid, p-toluenesulphonic acid) used alone or as a mixture, the deprotection being carried out in an organic solvent chosen from alcohols (methanol, ethanol, propanol, isopropanol), ethers (tetrahydrofuran, diisopropyl ether, methyl t-butyl ether), esters (ethyl acetate, isopropyl acetate, n-butyl acetate), aliphatic hydrocarbons (pentane, hexane, heptane), halogenated aliphatic hydrocarbons (dichloromethane, 1,2-dichloroethane), aromatic hydrocarbons (benzene, toluene, xylenes) and nitriles (acetonitrile) at a temperature between −10° and 60° C., preferably between 15° and 30° C. The inorganic or organic acid can be used in a catalytic or stoichiometric amount or in excess.

The deprotection can also be carried out under oxidizing conditions by using, for example, ammonium cerium(IV) nitrate in an acetonitrile/water mixture or 2,3-dichloro-5,6-dicyano-1,4-benzoquinone in a dichloromethane/water mixture.

The deprotection can also be carried out under reducing conditions, for example by hydrogenolysis in the presence of a catalyst.

The protective groups $G_1$ and $G_2$ are preferably 2,2,2-trichloroethoxycarbonyl, 2-(2-(trichloromethyl)-propoxy) carbonyl, benzyl, 4-alkoxybenzyl or 2,4-dialkoxybenzyl radicals in which the alkoxy radicals contain 1 to 4 carbon atoms or trialkylsilyl, dialkylarylsilyl, alkyldiarylsilyl or triarylsilyl radicals in which the alkyl parts contain 1 to 4 carbon atoms and the aryl parts are preferably phenyl radicals.

The replacement of the $G_1$ and optionally $G_2$ protective groups representing a silylated radical by hydrogen atoms can be carried out simultaneously with the deprotection of the side chain.

The replacement of the $G_1$ and optionally $G_2$ protective groups representing a 2,2,2-trichloroethoxycarbonyl or 2-(2-(trichloromethyl)propoxy)carbonyl radical is carried out with zinc, optionally in combination with copper, in the presence of acetic acid at a temperature between 20° and 70° C. or by means of an inorganic or organic acid such as hydrochloric acid or acetic acid in solution in an aliphatic alcohol containing 1 to 3 carbon atoms or in an aliphatic ester such as ethyl acetate, isopropyl acetate or n-butyl acetate in the presence of zinc, optionally in combination with copper.

The acids of general formula (I) are particularly useful for preparing the taxane derivatives of general formula (XXI) in which $R_4$ represents an acetyl radical, $R_1$ represents a benzoyl radical and Ar represents a phenyl radical (taxol) or else in which $R_4$ represents a hydrogen atom, $R_1$ represents a t-butoxycarbonyl radical and Ar represents a phenyl radical (Taxotere).

EXAMPLES

The following examples illustrate the present invention.

EXAMPLE 1

157 mg (0.40 mmol) of L-(+)-N-(4-methoxybenzyloxyacetyl)-2,10-camphorsultam and 1.5 cm³ of anhydrous tetrahydrofuran are introduced, under an argon atmosphere, into a 10 cm³ round-bottomed flask equipped with a magnetic stirrer system. The solution obtained is cooled to −30° C. and then 0.44 cm³ (0.44 mmol) of a 1M solution of lithium bis(trimethylsilyl)amide (LHMDS) in tetrahydrofuran is added dropwise. The mixture is allowed to react for 15 minutes at −30° C. and then 130 mg (0.63 mmol) of N-(t-butoxycarbonyl)benzylimine in solution in 1.0 cm³ of anhydrous tetrahydrofuran are added dropwise. The mixture is allowed to react for 15 minutes at −30° C. and then the reaction mixture is hydrolyzed at this temperature by addition of a saturated aqueous ammonium chloride solution. The temperature is allowed to rise to the region of 20° C. and the reaction mixture is then extracted twice with ethyl ether. The combined organic phases are washed 3 times with water, then once with a saturated aqueous sodium chloride solution and finally dried over anhydrous magnesium sulphate. After filtration and removal of the solvents under reduced pressure, there are obtained 290 mg of an oily residue which is purified by chromatography on a column of silica gel, the eluent being a hexane/ethyl acetate (85/15 by volume) mixture. There are thus obtained, with a yield of 60%, 146 mg (0.24 mol) of syn-L-(+)-N-[2-(4-methoxybenzyl)oxy-3-t-butoxycarbonylamino-3-phenylpropionyl]-2,10-camphorsultam, the characteristics of which are the following:

melting point: 85°–86° C.; optical rotation: $[\alpha]_D^{25}$=+ 54.7° (c=0.93, CHCl₃) infrared spectrum (film): characteristic absorption bands at 3425, 2950, 2920, 2850, 1720, 1710, 1610, 1580, 1510, 1490, 1385, 1360, 1325, 1270, 1240, 1210, 1160, 1130, 1100, 1055, 1030, 1005, 980, 900, 720 and 690 cm⁻¹; proton nuclear magnetic resonance spectrum (300 MHz, CDCl₃, chemical shifts in ppm, coupling constants J in Hz): 0.99 (s, 3H), 1.27 (s, 3H), 1.2–1.6 (m, 2H), 1.39 (s, 9H), 1.89–2.30 (m, 5H), 3.51 ($AB_q$, $J_{AB}$=13.6, $\delta_A$−$\delta_B$=21,7, 2H), 3.76 (s, 3H), 4.00 (distorted t, J=6.0 and 6.5, 1H), 4.29 ($AB_q$, $J_{AB}$=11.3, $\delta_A$−$\delta_B$=123.3, 2H), 4.83 (s, 1H), 5.31 (d, J=9.3, 1H), 5.57 (d, J=9.3, 1H), 6.68–6.74 (m, 2H), 6.89–6.95 (m, 2H), 7.20–7.43 (m, 5H); ¹³C nuclear magnetic resonance spectrum (50.3 MHz, CDCl₃ chemical shifts in ppm): 19.91 (CH₃), 20.58 (CH₃), 26.53 ($CH_2$), 28.18 ($CH_3$), 32.74 (($CH_2$), 37.49 ($CH_2$), 44.43 (CH), 47.85 (C), 48.81 (C), 53.04 ($CH_2$), 55.09 ($CH_3$), 55.64 (CH), 65.00 (CH), 72.11 ($CH_2$), 79.19 (C), 80.88 (CH), 113.39 (CH), 126.71 (CH), 127.05 (CH), 127.99 (CH), 128.77 (C), 129.46 (CH), 139.56 (C), 154.86 (C), 159.09 (C), 169.94 (C); mass spectrum (C.I., $NH_3$+isobutane): 599 ($MH^+$), 538, 499, 345, 233, 216, 206, 197, 180, 154, 150, 137, 121, 106; elemental analysis: ($C_{32}H_{42}N_2O_7S$); calculated C% 64.19 H% 7.07 N% 4.68 found 64.10 7.19 4.71

90 mg (0.15 mmol) of syn-L-(+)-N-[2-(4-methoxybenzyl) oxy-3-t-butoxycarbonylamino-3-phenyl-propionyl]-2,10-camphorsultam and 2.25 $cm^3$ of dry dichloromethane are introduced, under argon, into a 10 $cm^3$ single-necked flask equipped with a magnetic stirrer system. 15 grains of 4 Å molecular sieve and then 102 mg (0.45 mmol) of dichlorodicyanobenzoquinone are then added to the resulting solution using a solids charger. The reaction mixture is stirred for 14 hours at a temperature in the region of 20° C.

The reaction mixture is diluted in 40 $cm^3$ of dichloromethane. The organic phase is washed 3 times with 5 $cm^3$ of a saturated aqueous sodium bicarbonate solution, 3 times with 5 $cm^3$ of water, then once with a saturated aqueous sodium chloride solution and finally dried over anhydrous sodium sulphate. After filtration and removal of the solvent under reduced pressure, there are obtained 103 mg of an oily residue which is purified by chromatography on a column of silica gel, the eluent being an ethyl ether/dichloromethane (1/99 by volume) mixture. There are thus obtained, with a yield of 91%, 81 mg (0.136 mmol) of L-(+)-N-2,10-camphorsultam-(2R,4S,5R)-3-t-butoxycarbonyl-2-(4-methoxyphenyl)-4-phenyl-5-carbamoyl-1,3-oxazolidine, the characteristics of which are the following:

melting point: 147°–148° C.; optical rotation: $[\alpha]_D^{25}$=+52.90 (c=0.95, $CHCl_3$); infrared spectrum (film): characteristic absorption bands at 2970, 1710, 1620, 1595, 1520, 1460, 1395, 1375, 1345, 1300, 1280, 1250, 1225, 1170, 1140, 1095, 1070, 1030 and 830 $cm^{-1}$; proton nuclear magnetic resonance spectrum (300 MHz, $CDCl_3$, chemical shifts in ppm, coupling constants J in Hz): 0.85 (s, 3H), 0.90 (s, 3H), 1.01 (s, 9H), 1.26–1.52 (m, 2H), 1.84–1.87 (m, 3H), 2.07–2.10 (m, 2H), 3.33 (s, 2H), 3.75–3.88 (m, 1H), 3.81 (s, 1H), 5.16–5.27 (m, 2H), 6.28 (s, 1H), 6.89–6.92 (m, 2H), 7.20–7.40 (m, 5H), 7.50–7.53 (m, 2H); $^{13}C$ nuclear magnetic resonance spectrum (50.3 MHz, $CDCl_3$, chemical shifts in ppm): 19.54 ($CH_3$), 20.38 ($CH_3$), 26.07 ($CH_2$), 27.57 ($CH_3$), 32.38 ($CH_2$), 37.92 ($CH_2$), 44.42 (CH), 47.45 (C), 48.36 (C), 52.51 ($CH_2$), 55.06 ($CH_3$), 64.73 (CH), 65.31 (CH), 80.19 (C), 82.13 (CH), 92.41 (CH), 113.27 (CH), 126.58 (CH), 127.87(CH), 128.38 (CH), 129.02 (CH), 130.79 (C), 138.20 (C), 151.33 (C), 159.94 (C), 167.86 (C); elemental analysis ($C_{32}H_{40}N_2O_7S$); calculated C% 64.41 H% 6.76 N% 4.69 found 64.15 6.85 4.80

27 mg (0.045 mmol) of the amide obtained above and 0.7 $cm^3$ of a tetrahydrofuran/water (4/1 by volume) mixture are introduced, under argon, into a 10 $cm^3$ single-necked flask equipped with a magnetic stirrer system. The mixture is cooled to 0° C. and then 37 μl (0.36 mmol) of 30% by volume hydrogen peroxide and 7.9 mg (0.188 mmol) of lithium hydroxide hydrate ($LiOH.H_2O$) are added. The mixture is allowed to react for 30 minutes at 0° C. and is then stirred for 15 hours at 20° C.

On completion of the reaction, 10 $cm^3$ of dichloromethane, 10 $cm^3$ of water and then 57 mg (0.45 mmol) of sodium sulphite powder are added. The two phases are stirred vigorously. They are separated by settling and the basic aqueous phase is then washed 3 times with 10 $cm^3$ of dichloromethane. This aqueous phase is cooled to 0° C. and, with vigorous stirring and in the presence of 20 $cm^3$ of dichloromethane, it is acidified with a 1M aqueous hydrochloric acid solution to a pH of 1–2. It is then extracted 6 times with 15 $cm^3$ of dichloromethane. The combined organic phases are washed 3 times with 5 $cm^3$ of water and once with 5 $cm^3$ of a saturated aqueous sodium chloride solution and then dried over anhydrous magnesium sulphate. After filtration and removal of the solvents under reduced pressure, there are obtained, with a yield of 78%, 14 mg (0.0351 mmol) of (2R,4S,5R)-3-t-butoxycarbonyl-2-(4-methoxyphenyl)-4-phenyl-1,3-oxazolidine-5-carboxylic acid, the diastereoisomeric purity at C2 of which is greater than 97% and the characteristics of which are the following:

melting point: 140°–141° C.; infrared spectrum (film): characteristic absorption bands at 3700–2300, 2985, 2925, 1770, 1710, 1615, 1595, 1520, 1410, 1370, 1250, 1175, 1090, 1035, 920, 830, 730 and 700 $cm^{-1}$; proton nuclear magnetic resonance spectrum (200 MHz, $CDCl_3$, chemical shifts in ppm, coupling constants J in Hz): 1.06 (s, 9H), 3.81 (s, 3H), 4.61 (d, J=4.2, 1H), 5.40 (distorted d, J=4.7, 1H), 5.54 (very broad s, 1H), 6.38 (s, 1H), 6.89–6.95 (m, 2H), 7.26–7.42 (m, 7H); $^{13}C$ nuclear magnetic resonance spectrum (75.5 MHz, $CDCl_3$, chemical shifts in ppm): 27.79 ($CH_3$), 55.28 ($CH_3$), 63.67 (CH), 81.04 (C), 82.66 (CH), 92.39 (CH), 113.94 (CH), 126.33 (CH), 128.08 (CH), 128.37 (CH), 128.82 (CH), 130.51 (C), 140.42 (C), 151.71 (C), 160.43 (C), 172.67 (C); mass spectrum (C.I., $NH_3$+isobutane): 417 ($MH^+$+$NH_3$), 400 ($MH^+$), 361, 356, 344, 317, 300, 264, 256, 236, 213, 199, 180, 154, 137, 124, 110. elemental analysis ($C_{22}H_{25}NO_6$); calculated C% 66.15 H% 6.31 N% 3.51 found 66.01 6.35 3.56

L-(+)-N-(4-Methoxybenzyloxyacetyl)-2,10-camphorsultam can be prepared in the following way:

3.16 g (79 mmol) of 60% sodium hydride as a suspension in oil and 140 $cm^3$ of anhydrous tetrahydrofuran are introduced into a 500 $cm^3$ single-necked flask equipped with a magnetic stirrer system. The resulting suspension is cooled to 0° C. and then 3.036 g (22 mmol) of p-methoxybenzyl alcohol in solution in 70 $cm^3$ of anhydrous tetrahydrofuran are added to it. The reaction mixture is allowed to react for 30 minutes at 0° C. and then 4.6 g (33 mmol) of bromoacetic acid are introduced in small portions. The reaction mixture is heated at reflux of the solvent for 18 hours. The mixture is allowed to return to a temperature in the region of 20° C. and then the tetrahydrofuran is removed under reduced pressure. The residue obtained is dissolved in ethyl ether and the solution is poured into water cooled to 0° C. The resulting medium is acidified with a 10% aqueous hydrochloric acid solution. The two phases obtained are separated. The organic phase is washed twice with water, then once with a saturated aqueous sodium chloride solution and then it is dried over anhydrous magnesium sulphate. After filtration and removal of the solvent under reduced pressure, there are obtained 4.9 g of an oily residue which is purified by chromatography on a column of silica gel, the eluent being a hexane/ethyl acetate (50/50 by volume) mixture. There are obtained 4.3 g (22 mmol) of p-methoxybenzyloxyacetic acid, the characteristics of which are the following:

melting point: 54°–55° C.; infrared spectrum (film): characteristic absorption bands at 3600–2300, 2940, 1730, 1615, 1590, 1520, 1305, 1250, 1180, 1110, 1035 and 820 $cm^{-1}$; proton nuclear magnetic resonance spectrum (200 MHz, $CDCl_3$ chemical shifts in ppm, coupling constants J in Hz): 3.81 (s, 3H), 4.10 (s, 2H), 4.58 (s, 2H), 6.90 (d, J=8.6, 2H), 7.28 (d, J=8.6, 2H); $^{13}C$ nuclear magnetic resonance spectrum (50.3 MHz, CDCl$_3$, chemical shifts in ppm): 55.14 (CH$_3$), 66.06 (CH$_2$), 72.92 (CH$_2$), 113.86 (CH), 128.56 (C), 129.40 (C), 159.48 (C), 175.66 (C).

1.0 g (5.1 mmol) of the acid obtained above, 210 cm$^3$ of dry hexane and 0.4 cm$^3$ (380 mg, 5.2 mmol) of N,N-dimethylformamide are introduced, under argon, into a 500 cm$^3$ single-necked flask equipped with a magnetic stirrer system. 2.1 cm$^3$ (3.055 g, 24.07 mmol) of freshly distilled oxalyl chloride are then added to the resulting solution. The reaction mixture is allowed to react for 1 hour at a temperature in the region of 20° C. The organic phase is separated from an insoluble oily residue which is found at the bottom of the round-bottomed flask and the excess oxalyl chloride and the hexane are removed under reduced pressure. The resulting residue is purified by distillation under reduced pressure (0.01 mm of mercury, 0.013 kPa). There are thus obtained, with a yield of 79%, 863 mg (4.02 mmol) of the chloride of p-methoxybenzyloxyacetic acid, the characteristics of which are the following:

infrared spectrum (film): characteristic absorption bands at 2970, 2930, 2875, 1810, 1620, 1590, 1520, 1470, 1420, 1390, 1305, 1260, 1190, 1180, 1130, 1040, 940, 820, 770 and 750 cm$^{-1}$.

611 mg (2.84 mmol) of L-(+)-2,10-camphorsultam are dissolved in 6 cm$^3$ of anhydrous toluene in a 15 cm$^3$ round-bottomed flask equipped with a magnetic stirrer system. The solution is cooled to 0° C. and then 168 mg (4.2 mmol) of 60% sodium hydride as a suspension in oil are added. The reaction mixture is allowed to react for 30 minutes at a temperature in the region of 20° C. The reaction mixture is again cooled to 0° C. and then 763 mg (3.56 mmol) of the chloride of p-methoxybenzylacetic acid are added. The reaction mixture is allowed to return to a temperature in the region of 20° C. and is then allowed to react for 15 hours. On completion of the reaction, the resulting reaction mixture is diluted by addition of dichloromethane and then water is added very slowly. The organic phase is washed once with water, then once with a saturated aqueous sodium chloride solution and it is then dried over anhydrous magnesium sulphate. After filtration and evaporation of the dichloromethane under reduced pressure, there are obtained 1.34 g of an oily residue which is purified by chromatography on a column of silic gel, the eluent being a hexane/ethyl acetate (80/20 by volume) mixture. There are obtained, with a yield of 90%, 1.01 g (2.57 mmol) of L-(+)-N-[(4-methoxybenzyloxyacetyl)-2,10-camphorsultam, the characteristics of which are the following:

optical rotation: $[\alpha]_D^{25}$=+87.1° (c=3.25, CHCl$_3$); infrared spectrum (film): characteristic absorption bands at 2970, 1715, 1620, 1590, 1520, 1470, 1415, 1400, 1380, 1340, 1280, 1250, 1240, 1220, 1170, 1135, 1115, 1060, 1035, 985, 820 and 780 cm$^{-1}$; proton nuclear magnetic resonance spectrum (200 MHz, CDCl$_3$, chemical shifts in ppm, coupling constants J in Hz): 0.96 (8, 3H), 1.12 (s, 3H), 1.2–1.6 (m, 2H), 1.8–2.3 (m, 5H), 3.3–3.6 (m, 2H), 3.79 (s, 3H), 3.8–4.0 (m, 1H), 4.3–4.7 (m, 4H), 6.87 (d, J=8.6, 2H), 7.30 (d, J=8.6, 2H); $^{13}$C nuclear magnetic resonance spectrum (50.3 MHz, CDCl$_3$, chemical shifts in ppm): 19.62 (CH$_3$), 20.53 (CH$_3$), 26.18 (CH$_2$), 32.51 (CH$_2$), 37.98 (CH$_2$), 44.37 (CH), 47.57 (C), 49.02 (C), 52.41 (CH$_2$), 55.02 (CH$_3$), 64.73 (CH), 68.03 (CH$_2$), 73.00 (CH$_2$), 113.60 (CH), 129.01 (C), 129.60 (C), 159.21 (C), 168.82 (C); elemental analysis (C$_{20}$H$_{27}$NO$_5$S) calculated C% 61.07 H% 6.87 N% 3.56 found 61.23 7.05 3.62

EXAMPLE 2

5 mg (0.125 mmol) of sodium hydride, at 60% in mineral oil, in suspension in 2.5 cm$^3$ of anhydrous ether are placed, under an argon atmosphere, in a 10 cm$^3$ round-bottomed flask equipped with a magnetic stirrer system. 156 μl (172.8 mg, 1.251 mmol) of pure 4-methoxybenzyl alcohol are then added. The resulting homogeneous solution is stirred (evolution of gas) for 30 minutes at a temperature in the region of 20° C. and it is then cooled to 0° C. 125 μl (180 mg, 1.20 mmol) of trichloroacetonitrile are then added. The reaction mixture is allowed to react for 4 hours while allowing the temperature to slowly rise to the region of 20° C. The reaction mixture is concentrated under reduced pressure until an orange-yellow oil is obtained which is redissolved in 1.7 cm$^3$ of hexane containing 5.5 μl of dry methanol. The suspension is filtered through Celite under reduced pressure. The solids obtained are washed once with 5 cm$^3$ of hexane and the solvents are then removed under reduced pressure. The yellow oil obtained (4-methoxybenzyl trichloroacetimidate) is dissolved in 2 cm$^3$ of cyclohexane. 240 mg (0.81 mmol) of methyl (2R, 3S)-3-t-butoxycarbonylamino-3-phenyl-2-hydroxy-propionate, 1.0 cm$^3$ of dry dichloromethane and 4 μl of boron trifluoride etherate are then added. The reaction mixture is allowed to react at a temperature in the region of 20° C. for 13 hours. The reaction mixture is filtered through Celite and the solids are washed 3 times with 10 cm$^3$ of a dichloromethane/cyclohexane (1/2 by volume) mixture. The resulting organic phase is washed twice with 5 cm$^3$ of a saturated aqueous sodium hydrogencarbonate solution, 3 times with 5 cm$^3$ of water and once with 5 cm$^3$ of a saturated aqueous sodium chloride solution. It is dried over anhydrous magnesium sulphate. After filtration and evaporation of the solvents under reduced pressure, the residue obtained (547 mg) is purified by chromatography on a column of silica gel, the eluent being a hexane/ethyl acetate (70/30 by volume) mixture. There are obtained 282 mg of a solid which is recrystallized from the dichloromethane/hexane mixture at 0° C. After separation of the crystals obtained (impurities), the liquid phase ("mother liquors") is evaporated under reduced pressure. There are obtained, with a yield of 68%, 228 mg (0.55 mmol) of methyl (2R,3S)-3-t-butoxycarbonylamino-3-phenyl-2-[(4-methoxybenzyl)oxy]-propionate, the characteristics of which are the following:

melting point: 105°–106° C. (cyclohxane/dichloromethane); optical rotation $[\alpha]_D^{25}$=+37.60 (c=1.1, chloroform); infrared spectrum (film): characteristic absorption bands at 3440, 2970, 2950, 2840, 1760, 1720, 1620, 1590, 1455, 1420, 1395, 1370, 1215, 1170, 1110, 1030, 820 and 700 cm$^{-1}$; proton nuclear magnetic resonance spectrum (200 MHz, CDCl$_3$ chemical shifts in ppm, coupling constants J in Hz): 1.39 (s, 9H), 3.78 (s, 6H), 4.12 (d, J=2, 1H), 4.40 (AB$_q$, J$_{AB}$=11.4, $\delta_a$–$\delta_B$=78.3, 2H), 5.20 (distorted d, J=9, 1H), 5.60 (distorted d, J=9, 1H), 6.68–6.76, (m, 2H), 6.83–6.95 (m, 2H), 7.18–7.36 (m, 5H); $^{13}$C nuclear magnetic resonance spectrum (100 MHz, CDCl$_3$, chemical shifts in ppm): 28.18 (CH$_3$), 52.17 (CH$_3$), 55.16 (CH$_3$), 55.99 (CH), 72.37 (CH$_2$), 79.62 (C), 79.68 (CH), 113.58 (CH), 126.57 (CH), 127.32 (CH), 128.23 (CH), 128.58 (C), 129.54 (CH), 139.49 (C), 155.08 (C), 159.26 (C), 170.77 (C); mass spectrum (C.I., NH$_3$+isobutane): 433 (MH$^+$+NH3), 416 (MH$^+$), 377, 360, 354, 316, 206, 162, 138, 121, 106; elemental analysis (C$_{23}$H$_{29}$NO$_6$) calculated C% 66.49 H% 7.03 N% 3.37 found 66.27 7.07 3.31

130 mg (0.31 mmol) of the product obtained above and 4.5 cm$^3$ of dry dichloromethane are introduced, under an argon atmosphere, into a 15 cm$^3$ round-bottomed flask equipped with a magnetic stirrer system. 10 grains of 4Å molecular sieve and then 211 mg (0.93 mmol) of dichlorodicyanobenzoquinone are then added to the resulting solution using a solids charger. The reaction mixture is stirred for 16 hours at a temperature in the region of 20° C. The reaction mixture is diluted in 40 cm³ of dichloromethane. The organic phase is washed 3 times with 5 cm³ of a saturated aqueous sodium hydrogencarbonate solution, 3 times with 5 cm³ of water, then once with 5 cm³ of a saturated aqueous sodium chloride solution and dried over anhydrous sodium sulphate. After filtration and removal of the solvent under reduced pressure, there are obtained 130 mg of a residue which is purified by chromatography on a column of silica gel with an ethyl ether/hexane (20/80 by volume) mixture. There are thus obtained, with a yield of 66%, 85 mg (0.206 mmol) of pure (2R,4S,5R)-3-t-butoxycarbonyl-4-phenyl-2-(4-methoxyphenyl)-5-methoxycarbonyl-1,3-oxazolidine, the characteristics of which are the following:

melting point: 104°–105° C. (dichloromethane/hexane); optical rotation: $[\alpha]_D^{25}$=+58.80 (c=0.85, $CHCl_3$); infrared spectrum (film): characteristic absorption bands at 2970, 2950, 2920, 2840, 1765, 1740, 1710, 1620, 1590, 1520, 1395, 1385, 1375, 1255, 1175, 1140, 1030, 930 and 830 $cm^{-1}$; proton nuclear magnetic resonance spectrum (200 MHz, $CDCl_3$, chemical shifts in ppm, coupling constants J in Hz): 1.07 (s, 9H), 3.59 (s, 3H), 3.81 (s, 3H), 4.57 (d, J=4, 1H), 5.41 (broad s, 1H), 6.37 (broad s, 1H), 6.91 (d, J=8.8, 2H), 7.28–7.40 (m, 7H); $^{13}C$ nuclear magnetic resonance spectrum (50.3 MHz, $CDCl_3$): 27.81 ($CH_3$), 52.42 ($CH_3$), 55.27 ($CH_3$), 63.30 (CH), 80.64 (C), 83.00 (CH), 91.95 (CH), 113.63 (CH), 126.34 (CH), 127.92 (CH), 128.32 (CH), 128.72 (CH), 130.85 (C), 140.74 (C), 151.69 (C), 160.10 (C), 170.20 (C); mass spectrum (C.I., $NE_3$+ isobutane): 414 ($MH^+$), 375, 358, 314, 250, 206; elemental analysis ($C_{23}H_{27}NO_6$) calculated C% 66.81 H% 6.58 N% 3.39 found 66.85 6.56 3.45

42 mg (0.102 mmol) of the pure product obtained above and 4 cm³ of methanol are introduced, under an argon atmosphere, into a 15 cm³ round-bottomed flask equipped with a magnetic stirrer system. 2 cm³ of distilled water and 41.4 mg (0.3 mmol) of solid potassium carbonate are then added. The reaction mixture is allowed to react at a temperature in the region of 20° C. for 15 hours. On completion of the reaction, the methanol is removed under reduced pressure and then 10 cm³ of water are added. The basic aqueous phase is extracted 3 times with 10 cm³ of dichloromethane. This aqueous phase is then cooled to 0° C. and then, with vigorous stirring and in the presence of 20 cm³ of dichloromethane, it is acidified with a 1M hydrochloric acid solution to a pH=1–2. The acidic aqueous phase is extracted 5 times with 15 cm³ of dichloromethane. The combined organic phases are washed 3 times with 5 cm³ of water, once with 5 cm³ of a saturated aqueous sodium chloride solution and then dried over anhydrous magnesium sulphate. After filtration and removal of the solvents under reduced pressure, there are obtained, with a yield of 98%, 40 mg (0.1 mmol) of (2R,4S,5R)-3-t-butoxycarbonyl-2-(4-methoxyphenyl)-4-phenyl-1,3-oxazolidine-5-carboxylic acid, the characteristics of which are identical to those of the product obtained in Example 1.

EXAMPLE 3

104 mg (0.35 mmol) of methyl (2R,3S)-3-t-butoxycarbonylamino-3-phenyl-2-hydroxypropionate, 243 mg (1.6 mmol) of p-methoxyphenylmethyl methyl ether, 5 cm³ of acetonitrile freshly distilled over calcium hydride and a few grains of 4Å molecular sieve are introduced successively into a 10 cm³ round-bottomed flask equipped with a magnetic stirrer and fitted with a distillation system and a solids charger. The reaction mixture is heated to reflux and then 217 mg (0.96 mmol) of dichlorodicyanobenzoquinone are added in a single step using the solids charger. The reaction mixture is stirred for 10 minutes at reflux, the methanol formed being removed by distillation. The reaction mixture is diluted in dry dichloromethane and then filtered through Celite. The Celite is rinsed 4 times with dichloromethane. The combined organic phases are washed 3 times with a 5% (w/v) aqueous sodium bicarbonate solution, once with a saturated aqueous sodium chloride solution and then dried over anhydrous magnesium sulphate. After filtration and removal of the solvents under reduced pressure, there are obtained 331 mg of an oily residue which is purified by chromatography on a column of silica gel (silica impregnated with 2.5% (v/v) of triethylamine), the eluent being a hexane/ethyl acetate (95/5 by volume) mixture. There are thus obtained 136 mg of a "deliquescent" product which is recrystallized from a dichloromethane/hexane mixture. There are thus obtained, with a yield of 77%, 110 mg (0.27 mmol) of (2R,4S,5R)-3-t-butoxycarbonyl-4-phenyl-2-(4-methoxyphenyl)-1,3-oxazolidine, the characteristics of which are identical to those of the product obtained in Example 2.

EXAMPLE 4

0.29 g of L-(+)-N-(4-methoxybenzyloxyacetyl)-2,10-camphorsultam and 3 cm³ of tetrahydrofuran are introduced, under an argon atmosphere, into a 25 cm³ reactor equipped with a mechanical stirrer and a thermometer. 0.808 cm³ of a 1M solution of lithium bis(trimethylsilyl)amide in tetrahydrofuran is then added at −72° C. After stirring for 15 minutes, a solution of 0.2 g of N-benzoylbenzylimine in 1.5 cm³ of tetrahydrofuran is added. The reaction mixture is stirred for 45 minutes at −78° C. and is then hydrolyzed by addition of 0.6 cm³ of 10% hydrochloric acid. 10 cm³ of isopropyl ether and 2 cm³ of water are added. The pH of the reaction mixture is adjusted to 4 by addition of concentrated hydrochloric acid. The aqueous phase is separated by settling and the organic phase is then washed 3 times with 2 cm³ of water and once with 2 cm³ of a saturated aqueous sodium chloride solution. The organic phase is dried over anhydrous sodium sulphate. After filtration and concentration under reduced pressure, there is obtained 0.522 g of an oil which is purified by chromatography on 17 g of silica gel, the eluent being an ethyl acetate/heptane (30/70 by volume) mixture. There is thus obtained, with a yield of 80.8%, 0.35 g of L-(+)-N-[2-(4-methoxybenzyl)oxy-3-benzoylamino-3-phenylpropionyl]-2,10-camphosultam in the form of a syn/anti (85/15) mixture.

The product thus obtained is treated under the conditions described in Example 1 to give (2R,4S,5R)-3-benzoyl-2-(4-methoxyphenyl)-4-phenyl-1,3-oxazolidine-5-carboxylic acid.

N-Benzoylbenzylimine can be prepared in the following way:

A solution of 40.2 g of sodium phenylsulphinate in 200 cm³ of water is introduced into a 500 cm³ reactor equipped with a magnetic stirrer and a reflux condenser. A mixture of 12.35 g of benzamide and 21.22 g of benzaldehyde is then added. 60 cm³ of methanol are then added so as to obtain an off-white emulsion and then 7.54 cm³ of formic acid (d=1.22) are added. After stirring for 41 hours 30 minutes at a temperature in the region of 20° C., the mixture is heated for 3 hours at 65° C. After filtration through sintered glass No. 4, the product obtained is washed with twice 15 cm³ of isopropyl ether and then with twice 15 cm³ of water. After drying, there are obtained, with a yield of 15.6%, 5.48 g of N-(α-phenylsulphonyl-benzyl)benzamide.

15.4 g of N-(α-phenylsulphonylbenzyl)-benzamide are recovered from the filtration mother liquors.

The overall yield is in the region of 60%.

0.472 g of potassium carbonate is added to a solution of 1 g of the sulphone obtained above in 50 cm³ of tetrahydrofuran heated to 55° C. The mixture is heated at 55° C. for 3 hours 30 minutes and then for 2 hours 30 minutes at reflux. After cooling to a temperature in the region of 0° C., the precipitate formed is separated by filtration through sintered glass No. 4. The filtrate is concentrated to dryness and then taken up in 5 cm³ of isopropyl ether. The white precipitate which is formed is separated by filtration and then washed with isopropyl ether. 0.162 g of starting sulphone is thus recovered.

The filtrate, after concentrating to dryness, provides 0.46 g of N-benzoylbenzylimine, the structure of which is confirmed by the proton nuclear magnetic resonance spectrum.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for preparing a compound of the formula I:

wherein

Ar represents a phenyl or α- or β-naphthyl radical, $R_1$ represents an unsubstituted or substituted benzoyl radical or a radical $R_2$—O—CO in which $R_2$ represents an alkyl, cycloalkyl, bicycloalkyl, phenyl, or a saturated or unsaturated 5-6 membered nitrogenous heterocyclic radical which is unsubstituted or substituted by at least one alkyl radical having 1 to 4 carbon atoms, and Ph represents an unsubstituted or substituted phenyl radical, the process comprising:

a) reacting a formula II compound:

wherein

Ar, $R_1$, and Ph are defined as above, and

X represents a

residue of an optically active organic base or a residue —O—R in which R represents an alkyl radical having 1 to 4 carbon atoms and unsubstituted or substituted by a phenyl radical, in an organic solvent in the presence of dichlorodicyanobenzoquinone at a temperature between 0° C. and the boiling temperature of the reaction mixture, to obtain a compound of formula III:

wherein Ar, $R_1$, Ph, and X are defined as above; and b) hydrolyzing or saponifying the formula III compound to obtain the formula I compound.

2. Process according to claim 1, wherein the organic solvent is selected from ethers, esters, ketones, nitriles, optionally halogenated aliphatic hydrocarbons, and aromatic hydrocarbons.

3. Process according to claim 1 wherein the organic solvent is anhydrous.

4. Process according to claim 1, wherein the solvent is selected from ethers, esters, ketones, nitrites, optionally halogenated aliphatic hydrocarbons and optionally halogenated aromatic hydrocarbons.

5. Process according to claim 4, wherein the organic solvent is anhydrous.

6. Process according to claim 1 wherein the residue of the optically active organic base is a L-(+)-2,10-camphorsultam residue.

7. The process according to claim 1, wherein:

Ar is substituted with at least one substituent selected from a halogen atom selected from the group consisting of fluorine, chlorine, bromine, and iodine atoms, and alkyl, alkenyl, alkynyl, aryl, arylalkyl, alkoxy, alkylthio, aryloxy, arylthio, hydroxyl, hydroxyalkyl, mercapto, acylamino, aroylamino, alkoxycarbonylamino, amino, alkylamino, dialkylamino, carboxyl, alkoxycarbonyl, carbamoyl, dialkylcarbamoyl, cyano, $R_{10}CO$, wherein $R_{10}$ is hydrogen or the organic substituent of the OH of a carbonyl group radicals, and trifluoromethyl radicals, wherein the alkyl radicals and the alkyl portions of the other radicals have 1 to 4 carbon atoms, the alkenyl and alkynyl radicals have 2 to 8 carbon atoms, and the aryl radicals are phenyl or α- or β-naphthyl radicals;

$R_1$ represents an unsubstituted or substituted benzoyl radical or a radical $R_2$—O—CO— in which $R_2$ represents a straight or branched alkyl radical having 1 to 8 carbon atoms, a cycloalkyl radical having 3 to 6 carbon atoms, or a bicycloalkyl radical having 7 to 11 carbon atoms, these radicals unsubstituted or substituted with at least one substituent selected from a halogen atom, a hydroxyl radical, an alkyloxy radical having 1 to 4 carbon atoms, a dialkylamino radical in which each alkyl portion has 1 to 4 carbon atoms, a piperidino radical, a morpholino radical, a 1-piperazinyl radical (unsubstituted or substituted in position 4 with an alkyl radical having 1 to 4 carbon atoms or with a phenylalkyl radical in which the alkyl portion has 1 to 4 carbon atoms), a cycloalkyl radical having 3 to 6 carbon atoms, a phenyl radical, a cyano radical, a carboxyl radical, or an alkoxycarbonyl radical in which the alkyl portion has 1 to 4 carbon atoms, wherein the cycloalkyl, or bicycloalkyl radical is unsubstituted or substituted by at least one alkyl radical having 1 to 4 carbon atoms, or a phenyl radical unsubstituted or substituted with at least one substituent selected from an alkyl radical having 1 to 4 carbon atoms and an alkoxy radical having 1 to 4 carbon atoms; and Ph represents a phenyl radical substituted by at least one electron-donating radical selected from alkoxy radicals comprising 1 to 4 carbon atoms.

8. A process for preparing a compound of the formula I:

wherein

Ar represents a phenyl or α- or β-naphthyl radical, $R_1$ represents an unsubstituted or substituted benzoyl radical or a radical $R_2$—O—CO in which $R_2$ represents an alkyl, cycloalkyl, bicycloalkyl, phenyl, or a saturated or unsaturated 5-6 membered nitrogenous heterocyclic radical which is unsubstituted or substituted by at least one alkyl radical having 1 to 4 carbon atoms, and Ph represents an unsubstituted or substituted phenyl radical, the process comprising:

a) reacting a compound of the formula XIX:

wherein Ph is defined as above and $R_3$ represents an alkyl radical having 1 to 4 carbon atoms or an aryl radical, with a phenylisoserine compound of the formula XVI:

wherein Ar and $R_1$ are defined as above and R represents an alkyl radical having 1 to 4 carbon atoms unsubstituted or substituted by a phenyl radical, in an anhydrous medium in an organic solvent in the presence of dichlorodicyanobenzoquinone at a temperature between 0° C. and the boiling temperature of the reaction mixture, to obtain a compound of formula III:

wherein Ar, $R_1$, and Ph are defined as above and X represents a

residue of an optically active organic base or a residue —O—R in which R is defined as above; and b) saponifying the formula III compound in a basic medium to obtain the formula I compound.

9. The process according to claim 8, wherein:

Ar is substituted with at least one substituent selected from a halogen atom selected from the group consisting of fluorine, chlorine, bromine, and iodine atoms, and alkyl, alkenyl, alkynyl, aryl, arylalkyl, alkoxy, alkylthio, aryloxy, arylthio, hydroxyl, hydroxyalkyl, mercapto, acylamino, aroylamino, alkoxycarbonylamino, amino, alkylamino, dialkylamino, carboxyl, alkoxycarbonyl, carbamoyl, dialkylcarbamoyl, cyano, $R_{10}CO$, wherein $R_{10}$ is hydrogen or the organic substituent of the OH of a carbonyl group radicals, and trifluoromethyl radicals, wherein the alkyl radicals and the alkyl portions of the other radicals have 1 to 4 carbon atoms, the alkenyl and alkynyl radicals have 2 to 8 carbon atoms, and the aryl radicals are phenyl or α- or β-naphthyl radicals;

$R_1$ represents an unsubstituted or substituted benzoyl radical or a radical $R_2$—O—CO— in which $R_2$ represents a straight or branched alkyl radical having 1 to 8 carbon atoms, a cycloalkyl radical having 3 to 6 carbon atoms, or a bicycloalkyl radical having 7 to 11 carbon atoms, these radicals unsubstituted or substituted with at least one substituent selected from a halogen atom, a hydroxyl radical, an alkyloxy radical having 1 to 4 carbon atoms, a dialkylamino radical in which each alkyl portion has 1 to 4 carbon atoms, a piperidino radical, a morpholino radical, a 1-piperazinyl radical (unsubstituted or substituted in position 4 with an alkyl radical having 1 to 4 carbon atoms or with a phenylalkyl radical in which the alkyl portion has 1 to 4 carbon atoms), a cycloalkyl radical having 3 to 6 carbon atoms, a phenyl radical, a cyano radical, a carboxyl radical, or an alkoxycarbonyl radical in which the alkyl portion has 1 to 4 carbon atoms, wherein the cycloalkyl, or bicycloalkyl radical is unsubstituted or substituted by at least one alkyl radical having 1 to 4 carbon atoms, or a phenyl radical unsubstituted or substituted with at least one substituent selected from an alkyl radical having 1 to 4 carbon atoms and an alkoxy radical having 1 to 4 carbon atoms; and Ph represents a phenyl radical substituted by at least one electron-donating radical selected from alkoxy radicals having 1 to 4 carbon atoms.

* * * * *